US006472182B1

(12) United States Patent
Kobayashi et al.

(10) Patent No.: US 6,472,182 B1
(45) Date of Patent: Oct. 29, 2002

(54) PROCESS FOR PRODUCING TRANSGLUTAMINASE BY MICROORGANISM

(75) Inventors: Katsunori Kobayashi; Shigeru Yamanaka; Yuko Tanita; Naoko Tsuyoshi; Ryosuke Fudo; Junko Shinozaki; Kenzo Yokozeki; Shunichi Suzuki, all of Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 08/952,959

(22) PCT Filed: Jun. 10, 1996

(86) PCT No.: PCT/JP96/01569

§ 371 (c)(1),
(2), (4) Date: Dec. 4, 1997

(87) PCT Pub. No.: WO96/41866

PCT Pub. Date: Dec. 27, 1996

(30) Foreign Application Priority Data

Jun. 8, 1995 (JP) ........................................ 7-141824
Aug. 4, 1995 (JP) ........................................ 7-199487

(51) Int. Cl.[7] ........................ C12P 21/04; C12N 9/10
(52) U.S. Cl. .................. 435/71.1; 435/71.2; 435/68.1; 435/193
(58) Field of Search ............................ 435/193, 68.1, 435/71.1, 71.2

(56) References Cited

U.S. PATENT DOCUMENTS 5,156,956 A 10/1992 Motoki et al.
5,420,025 A 5/1995 Takagi et al.
5,514,573 A 5/1996 Yasueda et al.
5,607,849 A 3/1997 Yasueda et al.
5,731,183 A 3/1998 Kobayashi et al.
5,736,356 A 4/1998 Sano et al.

FOREIGN PATENT DOCUMENTS

CH 1084888 A 4/1994
DK WO 96/06931 3/1996
DK WO 96/22366 7/1996

OTHER PUBLICATIONS

Barnett et al., "Yeasts", Cambridge University Press, 1983, pp. 231, 528.*

Ando, H. et al.: "Purification and characteristics of a novel transglutaminase derived from microorganisms" Agricultural and Biological Chemistry, vol. 53, No. 10, 1989, pp. 2613–2617 XP000876646 the whole document*.

Klein, J.D.: "Purification and partial characterization of transglutaminase from Physarum polycephalum" Journal of Bacteriology, vol. 174, No. 8, Apr. 1992, pp. 2599–2605, XP000878763 *the whole document*.

Ramanujam, M.V. and Hageman, J.H.: "Intracellular transglutaminase (EC 2, 3, 2.13) in a procaryote: Evidence from vegetative and sporulating cells of *Bacillus subtillis* 168" FASEB Journal, vol. 4, No. 7, 1990, p. A2321 XP002099267 *the whole document*.

Lorand, L. et al.: "Role of the intrinsic transglutaminase in the Ca2+–mediated crosslinking of erythrocyte proteins" Proc. Natl. Acad. Sci. USA, vol. 73, No. 12, Dec. 1976, pp. 4479–4481, XP000985121 *the whole document.

Ruiz–Herrera J., "Involvement of transglutaminase in the formation of covalent cross–link in the cell wall of Candida albicans." Arch. Microbiol. Springer), 1995, vol. 164, No. 3, pp. 186–193.

Muriel P., "Damine Oxidase and Transglutaminase Activities in White lupine Seedlings with Respect to Cross–linking of Proteins." J. Agric. Food Chem., 1995, vol. 43, pp. 1151–1156.

* cited by examiner

*Primary Examiner*—Irene Marx
(74) *Attorney, Agent, or Firm*—Oblon, Spivak, McClelland, Maier & Neustadt, P.C.

(57) ABSTRACT

The present invention provides a process for producing a transglutaminase, which comprises culturing microorganisms of any of the genus Micrococcus, Clostridium, Torulopsis, Rhizopus and Monascus in a medium to produce the intended transglutaminase in the medium or in the cells of the microorganisms and then isolating the transglutaminase, and a process for producing a gelled proten with the thus-obtained transglutaminase. According to the process of the present invention, transglutaminase can be rapidly produced at a low cost.

4 Claims, 13 Drawing Sheets

Effect of protease inhibitor on Putrescine-incorporating activity

Effect of protease inhibitor on protease activity of α-chymotripsin and the culture supernatant liquid of Aspergillus oryzae

PROCESS FOR PRODUCING TRANSGLUTAMINASE BY MICROORGANISM

TECHNICAL FIELD

The present invention relates to a process for producing transglutaminase (hereinafter referred to as "TG") from microorganisms such as bacteria, molds and yeasts, and also a process for producing gelled proteins with TG thus obtained.

TG is an enzyme which catalyzes an acyl transfer reaction of a γ-carboxyamide group in a glutamine residue in a peptide chain. When TG reacts with ane-amino group of a lysine residue in protein as an acyl acceptor, an ϵ-(γ-Glu)-Lys crosslinking bond is formed in the molecule and between the molecules. When water functions as the acyl acceptor, this enzyme facilitates the deamidation reaction of a glutamine residue to form a glutamic acid residue.

TG produced by the present invention is usable for the production of a gelled protein, which is usable as a gel food, gelled cosmetic, etc. like a known TG derived from Actinomyces.

BACKGROUND OF THE INVENTION

It has been known hitherto that TG is contained in various animal tissues. For example, TG is contained in the liver of a guinea pig and investigations are made thereon [Connellan et al., Journal of Biological Chemistry, Vol. 246,1093–1098 (1971)]. However, as for TG produced from microorganisms, only those produced by Actinomyces and *Bacillus subtilis* (M. V. Ramanujam et al., FASEB J. Vol. 4, A2321) and Myxomycetes (J. D. Klein et al., J. Bacteriol. Vol. 174, 2599 to 2605) were reported.

At present, TG produced by Actinomyces is practically used on an industrial scale [Japanese Patent Unexamined Published Application (hereinafter referred to as "J. P. KOKAI") No. Sho 64–27471].

The utilization of TG derived from animals for the industry, particularly for the production of a gelled protein, has the following defects:

(1) It is difficult to obtain a large amount of TG derived from animals at a low cost.

(2) The uses of TG are limited, since it demands calcium ion.

TG derived from Actinomyces has a defect that since the growing rate of Actinomyces microorganisms is usually lower than that of bacteria, a long culture time is necessitated, so that it results in increase of the production cost.

DISCLOSURE OF THE INVENTION

As for the practical use of TG derived from animals, such a use has never been expected because the calcium-demanding properties thereof limit the uses thereof and the mass production thereof at a low cost is impossible. TG derived from Actinomycetes has a lower growth rate than that from bacteria and is disadvantageous from the view-point of costs.

Therefore, the object of the present invention is to provide a new process for producing TG with microorganisms usually used for foods from old times at a high growth rate and at a reasonable cost.

After intensive investigations made for the purpose of solving the above-described problems, the inventors have found that specified microorganisms produce TG in the course of the culture thereof or they accumulate TG in their cells. The present invention has been completed on the basis of this finding.

Namely, the present invention provides a process for producing a transglutaminase, which comprises culturing microorganisms of any of the genus Micrococcus, Clostridium, Candida, Rhizopus and Monascus in a medium to produce the intended transglutaminase in the medium or in the cells of the microorganisms and then isolating the transglutaminase, and also a process for producing a gelled protein with the thus-obtained TG.

BEST MODE FOR CARRYING OUT THE INVENTION

Figure 1:
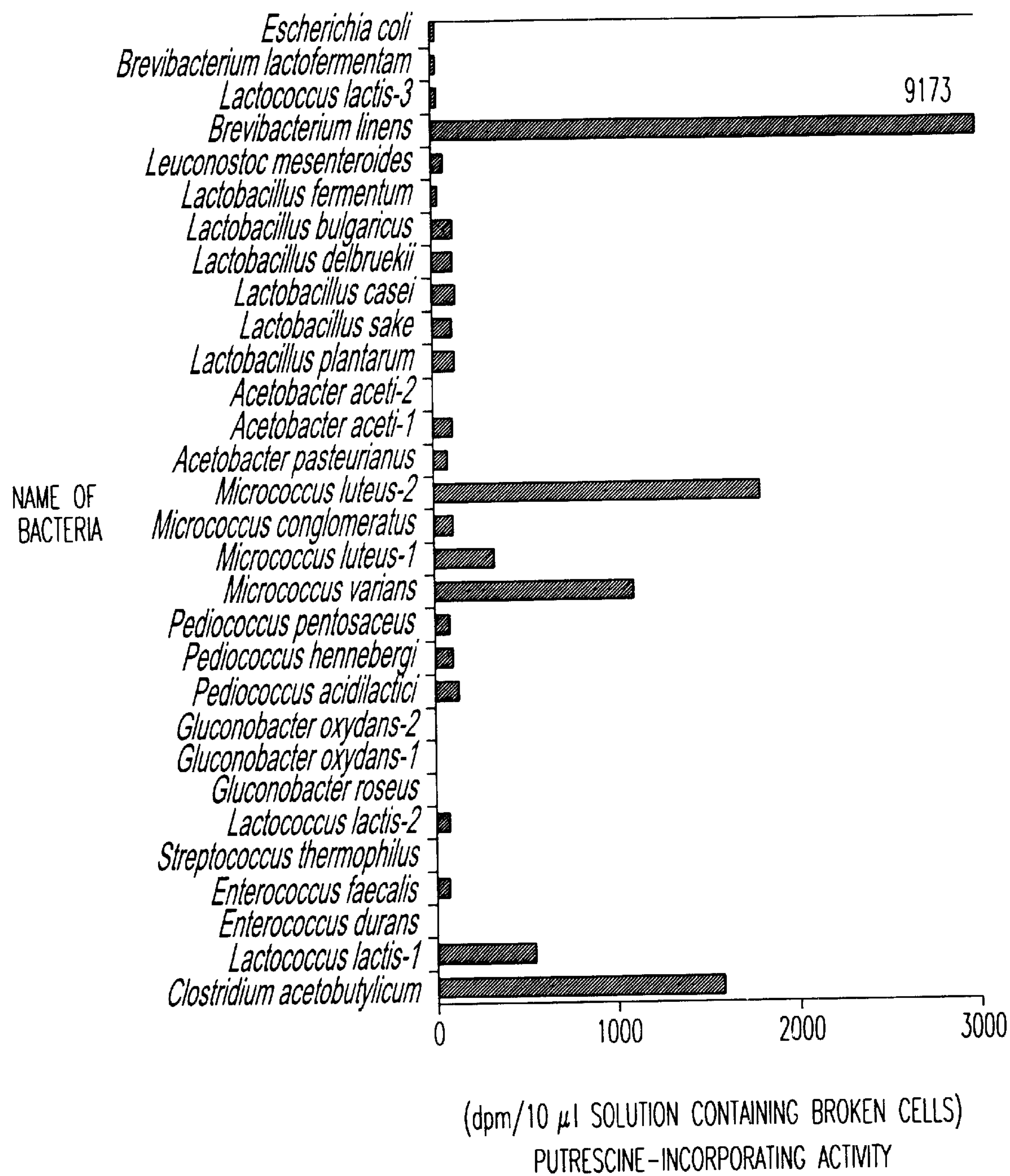
FIG. 1 shows putrescine-incorporating activity of bacteria used for foods and also bacteria of the same genus in the solid culture.

The term "TG" herein indicates an enzyme which catalyzes an acyl transfer reaction of a γ-carboxyamide group in a glutamine residue in a peptide chain. When TG reacts on ane-amino group of a lysine residue in protein as an acyl acceptor, an ϵ-(γ-Glu)-Lys crosslinking bond is formed in the molecule and between the molecules.

In the present invention, the transglutaminase is preferably obtained by culturing the above-specified microorganism in a medium to produce the intended transglutaminase in the medium or in the cells, then (1) isolating transglutaminase from the medium or (2) breaking the cells or by lysis, and then solubilizing the product, if necessary.

After intensive investigations on the TG activity of mainly each of bacteria, yeasts, fungi, etc. used for producing foods from old times in the culture liquid or cells, the inventors have found some strains having the TG activity.

The description will be made below on examples of the bacteria having the TG activity in the cells or culture liquid thereof.

Bacteria of the genus Micrococcus and Clostridium, which are usable for foods, are preferred. In particular, *Micrococcus luteus* and *Clostridium acetobutylicum* are preferred. Specifically, *Micrococcus luteus* ATCC 400 and *Clostridium acetobutylicum* ATCC 4259 are preferred.

Then the description will be made below on examples of the yeasts having the TG activity in the cells or culture liquid thereof.

Yeasts of the genus Candida, which are usable for foods, are preferred. In particular, *Candida versatilis* is preferred. Specifically, *Candida versatilis* NRRL Y-6652 is preferred.

The description will be made below on examples of the fungi having the TG activity in the cells or culture liquid thereof.

Fungi of the genus Rhizopus and Monascus, which are usable for foods, are preferred. In particular, *Rhizopus oryzae, Rhizopus chinensis, Rhizopus delemar, Rhizopus javanicus* and *Monascus purpureus* are preferred.

Specifically, *Rhizopus oryzae* FERM BP-5546 and FERM BP-5549, *Rhizopus chinensis* JCM 5596, *Rhizopus delemar* JCM 5564, *Rhizopus javanicus JCM* 5574 and *Monascus purpureus* ATCC 16360 are usable. "JCM" is an abbreviation of Japan Collection of Microorganisms (the same shall apply hereinafter).

Then, the description will be made on the methods for the culture of the microorganisms and purification to obtain TG. In carrying out the present invention, the culture form can be either liquid culture or solid culture. When the culture is conducted on an industrial scale, the aerated culture under stirring is advantageous.

The nutrients in a nutrient medium used include carbon sources, nitrogen sources, inorganic acids and other minor nutrients usually used for the culture of microorganisms. In addition, nutrients utilizable by the microorganisms are available.

The culture conditions of (1) bacteria and yeasts are slightly different from those of (2) fungi. The description will be made on the culture conditions of (1) bacteria and yeasts at first.

The bacteria and yeasts are cultured under aerobic conditions at a culture temperature in such a range that they can grow to produce TG. However, those which can be cultured by anaerobic culture may be cultured under anaerobic conditions.

Although the conditions are thus not strictly limited, the culture temperature is usually 10 to 50°, and preferably 25 to 40°. The culture time which varies depending on the temperature and other conditions is such that the maximum amount of TG is produced. The culture time is usually 5 hours to 14 days, preferably about 10 hours to 7 days.

The description will be made on the fungi.

The fungi are cultured under aerobic conditions at a culture temperature in such a range that they can grow to product TG. The culture temperature is usually 10 to 50°, and preferably 20 to 35°. The culture time which varies depending on the culture conditions is such that the maximum amount of TG is produced. The culture time is usually 1 to 20 days, preferably 2 to 14 days.

After the completion of the culture, solids are removed from the culture liquid by the filtration and TG accumulated in the culture liquid is obtained from the filtrate. Pure TG can be obtained from the culture filtrate by any of ordinary methods for purifying enzymes.

Pure TG can be obtained by, for example, the treatment with an organic solvent such as ethanol, acetone or isopropyl alcohol, salting out with ammonium sulfate, common salt or the like, dialysis, ultrafiltration, ion exchange chromatography, adsorption chromatography, gel filtration, adsorption with an adsorbent, and isoelectric point fractionation. When the degree of purification of TG is elevated by suitably combining these methods, the combination is also possible.

A salt, saccharide, lipid, protein, surfactant or the like may be added, if necessary, as the stabilizer to the enzyme solution obtained as described above, and then the solution is subjected to the ultrafiltration concentration, reverse osmosis concentration, reduced pressure drying, freeze drying, spray drying or the like to obtain the purified, liquid or solid TG.

TG accumulated in the cells is collected by recovering the cells from the culture liquid after the completion of the culture. After the breakage or lysis (bacteriolysis) of the cells, the product thus obtained can be used as the gelling agent as it is or after the concentration.

The destruction can be conducted by various methods such as ultrasonic treatment, grinding with beads or the like, destruction by pressure and destruction by freezing.

It is also possible, if necessary, to recover the TG activity in a soluble fraction by solubilizing the treated cells by various solubilizing methods. For example, (1) the cells can be solubilized by treating them with a surfactant such as Triton X-100 or an alkyl glucoside. (2) The active fraction can be solubilized by further treating the treated cells with an acidic or basic buffer solution. (3) The treated cells can be solubilized by suspending them in a buffer solution and elevating the temperature to, for example, 10° or above. TG thus solubilized by various methods is also usable as the gelling agent.

Purified TG having a higher specific activity can be obtained from the solubilized TG-containing solution by any method usually employed for the purification of enzymes as the above-described purification of TG from the culture liquid. The gelling agent TG having a higher efficiency can be thus obtained.

The TG activity was determined by determining the putrescine-incorporating activity into dimethylcasein (hereinafter referred to as putrescine-incorporating activity) as described below. The reaction was conducted by using putrescine labelled with $^{14}C$ and dimethylcasein as the substrate. Dimethylcasein bonded with putrescine is precipitated with 10% TCA and the precipitate is adsorbed on a filter paper. The radiation activity of the filter paper thus treated is measured with a liquid scintillation counter or the like to conduct the determination.

However, the incorporation of putrescine into dimethylcasein is a reaction caused also by the dehydration bonding of protease or transition reaction. Therefore, there is a possibility of detecting the protease activity as the TG activity.

Thus, the real TG activity can be confirmed by examining the inhibition of the putrescine incorporation activity by a protease inhibitor. Namely, when the putrescine-incorporating activity of a sample is not inhibited by the protease inhibitor, the TG activity thereof is the real one. The details of the confirmation of the real TG activity are described in Examples described below.

Therefore, the present invention provides a method for screening a transglutaminase-producing microorganism, which comprises reacting a microorganism sample with a substrate containing $^{14}C$-labelled putrescine and dimethylcasein in the absence of a protease inhibitor, to select the microorganism which produces dimethylcasein bonded with putrescine, then conducting the same reaction with a substrate containing $^{14}C$-labelled putrescine and dimethylcasein in the presence of a protease inhibitor selected from among soybean Bawman-Birk inhibitor, chymostatin and ovoinhibitor, comparing an amount of the product obtained by the reaction conducted in the presence of the protease inhibitor with that of dimethylcasein bonded with putrescine obtained by the reaction conducted in the absence of the protease inhibitor, and selecting the microorganism capable of producing dimethylcasein bonded with putrescine obtained in an amount which is substantially not reduced in the presence of each protease inhibitor. There is preferably taken a microorganism capable of producing at least 65 parts, desirably 75 to 100 parts, of dimethylcasein bonded with putrescine in the presence of each of the above-described protease inhibitor, for 100 parts of dimethylcasein bonded with putrescine produced by the culture in the absence of the protease inhibitor. Namely, a microorganism capable of producing at least 65 parts of dimethylcasein bonded with putrescine under each of three culture conditions (i.e. in the presence of each of soybean Bawman-Birk inhibitor, chymostatin and ovoinhibitor) is selected.

In this process, the microorganism to be tested is cultured under optimum conditions. The amount of the $^{14}C$-labelled putrescine is preferably 1 to 2,000 nmol and that of dimethylcasein is preferably 1 to 200 mg/ml in the substrate. The culture time is preferably about 1 minute to 6 hours.

The description will be made on another embodiment of the present invention, i.e. process for producing gelled protein with TG. Gelled protein can be produced by a process disclosed in Japanese Patent Publication for Opposition Purpose (hereinafter referred to as "J. P. KOKOKU") No. Hei 6-65280 and J. P. KOKAI No. Hei 6-225775, the disclosures which are incorporated herein by reference.

TG usable for the production of the gelled protein includes purified TG, a culture solution having TG activity, and a fraction having TG activity which is obtained by breaking or lysis of the cells having TG activity. Further, the above-described soluble fraction is also usable. Namely, any fraction having TG activity is usable.

The origin and properties of the protein usable as the substrate are not limited so far as it has both lysine residue and glutamine residue and so far as it is reactive with the above-described catalyst. Further, peptides partially cut with a protease or the like, synthetic peptides and chemically modified various proteins are also usable as the substrates of the enzyme so far as they contain lysine residue and glutamine residue.

When TG obtained by the present invention is added to a liquid or slurry containing such a protein to conduct the reaction, 1) a product having a high viscosity or in the form of a gel is obtained when the protein concentration is high, or 2) a cross-linked high-molecular product in the form of a solution or precipitate is obtained when the protein concentration is low. As for the reaction conditions, the pH of the reaction solution is about 4 to 10, reaction temperature is about 5 to 80° and the reaction time is about 10 seconds to 24 hours in general.

The degree of crosslinking is variable by selecting the kind of the protein and the amount thereof and, therefore, the properties and water content of the gel to be obtained are variable depending on the purpose and use.

The following Examples will further illustrate the present invention, which by no means limit the technical range of the present invention.

EXAMPLE 1

In this Example, the following strains of bacteria usable for foods were used.

TABLE 1

| Strain | Deposit |
|---|---|
| *Lactococcus lactis* (1) | FERM P-14972 |
| *Lactococcus lactis* (2) | AJ11145 |
| *Lactococcus lactis* (3) | AJ5805 |
| *Enterococcus durans* | AJ3805 |
| *Enterococcus faecalis* | ATCC12984 |
| *Streptococcus thermophilus* | AJ3809 |
| *Gluconobacter roseus* | IAM1838 |
| *Gluconobacter oxydans* (1) | IFO3172 |
| *Gluconobacter oxydans* (2) | IFO3189 |
| *Pediococcus acidilactici* | ATCC8042 |
| *Pediococcus hennebergi* | AJ3157 |
| *Pediococcus pentosaceus* | IFO3182 |
| *Micrococcus varians* | IAM1314 |
| *Micrococcus luteus* (1) | ATCC400 |
| *Micrococcus luteus* (2) | IFO3333 |
| *Micrococcus conglomeratus* | AJ1062 |
| *Acetobacter pasteurianus* | FERM P-14973 |
| *Acetobacter aceti* (1) | IFO3281 |
| *Acetobacter aceti* (2) | IFO3288 |
| *Lactobacillus plantarum* | ATCC8014 |
| *Lactobacillus sake* | ATCC9338 |
| *Lactobacillus casei* | ATCC7469 |
| *Lactobacillus delbruekii* | ATCC9649 |
| *Lactobacillus bulgaricus* | ATCC11842 |
| *Lactobacillus fermentum* | JCM1173 |
| *Leuconostoc mesenteroides* | FERM P-14974 |
| *Escherichia coli* | ATCC27325 |
| *Brevibacterium lactofermentum* | ATCC13869 |
| *Brevibacterium linens* | ATCC9172 |
| *Clostridium acetobutylicum* | ATCC4259 |

In the above Table, AJ and IAM are abbreviations of Central Research Laboratories, Ajinomoto Co. Inc. and IAM Culture Collection, respectively (the same shall apply hereinafter).

The solid culture or liquid shaking culture of the strains listed above was conducted with Trypticase soy medium, acetic acid bacteria medium, MRS medium or the like. In the solid culture, a proper amount of the cells were collected after the culture for 2 to 4 days.

Bacteria of the genus Clostridium were cultured by feeding 5 ml of a medium [comprising 5 g, per liter of the medium, of glucose, 0.9 g of $(NH_4)_2SO_4$, 0.45 g of $KH_2PO_4$, 0.075 g of $K_2HPO_4$, 0.09 g of $MgSO_4.7H_2O$, 0.9 g of NaCl, 0.09 g of $CaCl_2.2H_2O$, 10 g of trypticase (BBL), 5 g of a yeast extract (Difco), 2 g of a meat extract (Difco), 0.007 g of Hemin, 4 g of $Na_2CO_3$, 0.3 g of L-cysteine.HCl.$H_2O$ and 0.001 g of Resazurin, pH 7.2] into a 20 ml test tube, then controlling the composition of the gas phase to $N_2/CO_2/H_2O$=80/10/10, inoculating the bacteria and conducting the culture under anaerobic conditions at 37°.

In the liquid culture, 10 ml of the culture liquid was taken and centrifuged in the logarithmic growth phase (referred to as "log" in the figures) (attained after the culture for about 3 to 5 hours) and also 0, 5, 10 and 20 hours after the start of the stationary phase (attained after the culture for about 6 to 10 hours) to obtain the precipitates and the supernatant liquid. The cells obtained as the precipitates were suspended in 1 ml of Tris buffer solution (20 mM Tris, pH 7.5) and broken with glass beads. The suspension containing the broken cells and supernatant culture liquid were used as the samples to be tested.

In the solid culture, the bacteria were cultured in an agar-containing medium for 2 to 4 days and then a proper amount of the cells was collected. The cells were taken by scraping with a platinum loop. A suitable amount of the cells thus obtained was suspended in 1 ml of Tris buffer solution (20 mM Tris, pH 7.5) and broken with glass beads. The suspension containing the broken cells and supernatant culture liquid were used as the samples to be tested.

The TG activity was determined by measuring the putrescine-incorporating activity. 50 $\mu$l of the reaction liquid (100 mM Tris buffer solution having pH 7.5 and containing 6.3 mg/ml of dimethylcasein and 10 nM of $^{14}$C-putrescine 1.2 $\mu$Ci) containing 10 $\mu$l of the test sample was reacted at 37° for 30 minutes and then 40 $\mu$l of the reaction product was adsorbed on a filter paper and fixed with 10% TCA. After washing with 5% TCA solution three times, the radioactivity of the product was determined with a liquid scintillation counter to determine the putrescine-incorporating activity. The results of the determination of the strain samples are shown in FIGS. 1 to 3.

Figure 2:
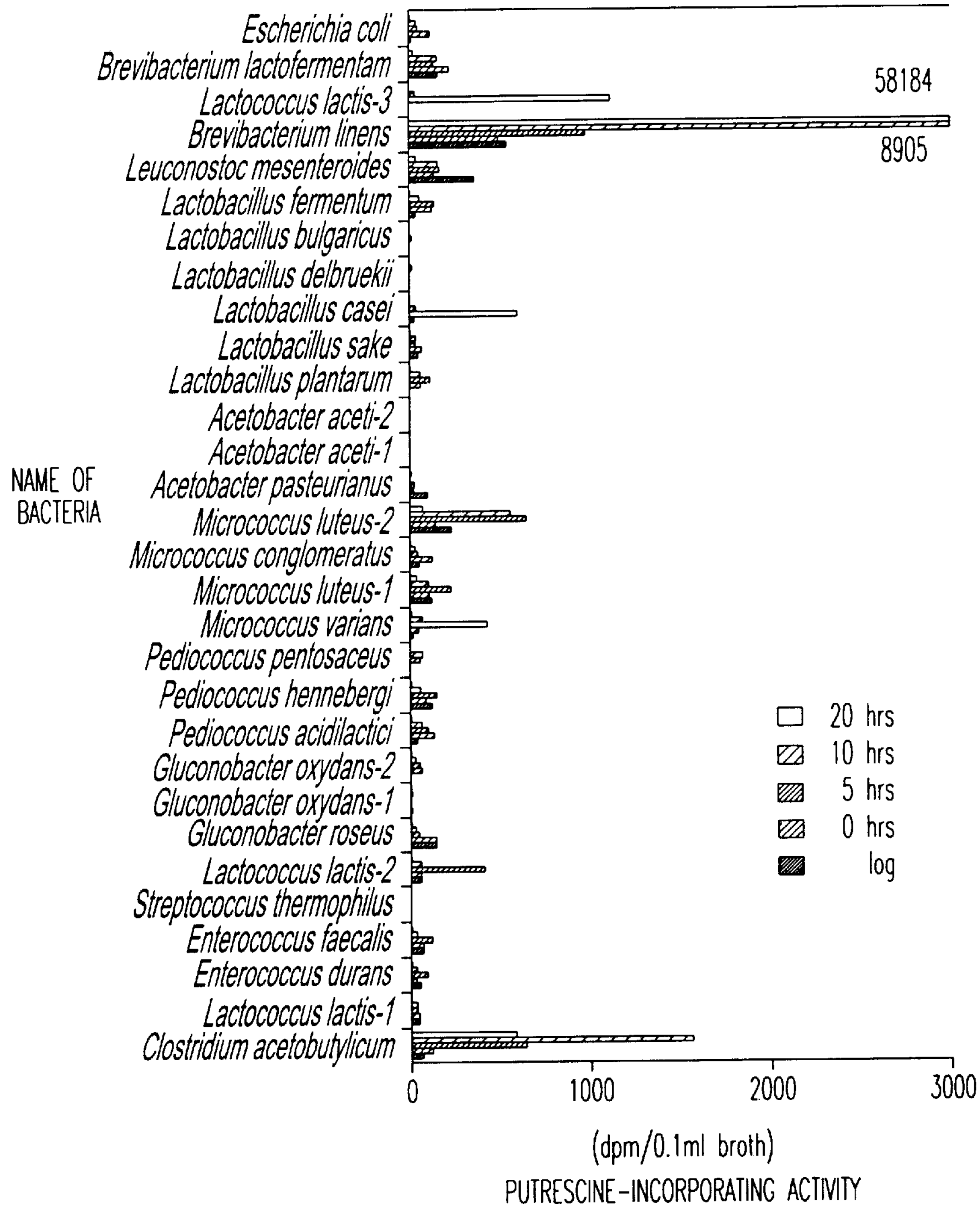
FIG. 2 shows putrescine-incorporating activity of bacteria used for foods and also bacteria of the same genus in the liquid culture.
Figure 3:
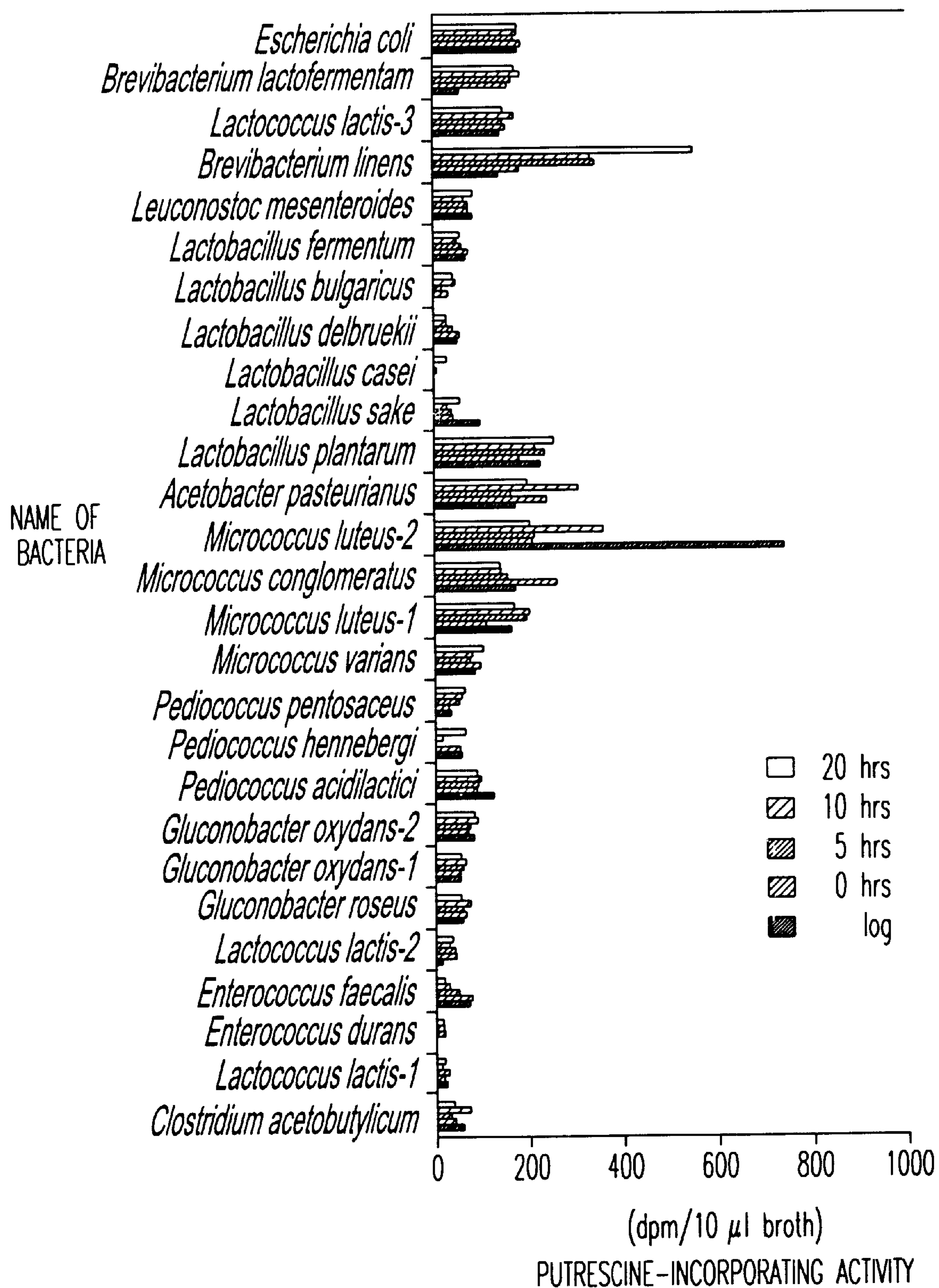
FIG. 3 shows the activity of incorporating putrescine in a supernatant liquid in the liquid culture of bacteria used for foods and also bacteria of the same genus.

As shown in FIGS. 1 to 3, the putrescine-incorporating activity was recognized in the cells of bacteria of the genus Lactococcus, Enterococcus, Gluconobacter, Pediococcus, Micrococcus, Acetobacter, Lactobacillus, Leuconostoc, Brevibacterium, Escherichia or Clostridium or in the culture liquid thereof.

Among them, *Brevibacterium linens, Micrococcus luteus, Lactococcus lactis, Lactobacillus casei, Enterococcus faecalis, Gluconobacter oxydans, Pediococcus pentosaceus, Acetobacter pasteurianus, Leuconostoc mesenteroides, Escherichia coli* and *Clostridium acetobutylicum* had a relatively high putrescine-incorporating activity.

EXAMPLE 2

In this Example, strains of yeasts or the like usable for various foods, shown in the following Table 2, were used.

TABLE 2

| | |
|---|---|
| *Candida versatilis* | NRRL Y-6652 |
| *Debaryomyces hansenii* | IFO0644 |
| *Pichia anomala* (1) | IFO0130 |
| *Pichia anomala* (2) | IFO0144 |
| *Saccharomycopsis fibuligera* | IFO0103 |
| *Saccharomyces carlsbergensis* | CBS1513 |
| *Saccharomyces bayanus* (1) | CBS395 |
| *Saccharomyces bayanus* (2) | CBS380 |
| *Saccharomyces florentinus* | AJ4100 |
| *Saccharomyces chevalieri* | CBS400 |
| *Saccharomyces cerevisiae* | CBS1171 |
| *Zygosaccharomyces rouxii* (1) | CBS726 |
| *Zygosaccharomyces rouxii* (2) | IFO0495 |
| *Zygosaccharomyces mrakii* | CBS4218 |
| *Zygosaccharomyces thermotolerans* | CBS6340 |
| *Torulaspora delbruekii* (1) | IFO1129 |
| *Torulaspora delbruekii* (2) | CBS817 |
| *Kluyveromyces marxianus* | IFO0288 |

In the above Table, CBS is an abbreviation of Centraalbureau voor Schimmelcultures.

The bacteria of each strain described above were cultured by the liquid shaking culture with YM medium or the like at 28° C. 10 ml of the culture liquid was taken and centrifuged in the logarithmic growth phase (attained after the culture for about 3 to 6 hours), at the start of the stationary phase (attained after the culture for about 6 to 12 hours) (namely, after 0 day) and on the second and fourth days to obtain the precipitates and supernatant liquid. The cells obtained as the precipitates were suspended in 1 ml of Tris buffer solution (20 mM Tris, pH 7.5) and broken with glass beads. The suspension containing the broken cells and supernatant culture liquid were subjected to the test of the putrescine-incorporating activity in the same manner as that of Example 1.

The solid culture was also conducted in the same manner as that of Example 1, and the thus-obtained product was also used as the test sample for the putrescine-incorporating activity conducted in the same manner as that of Example 1.

Figure 4:
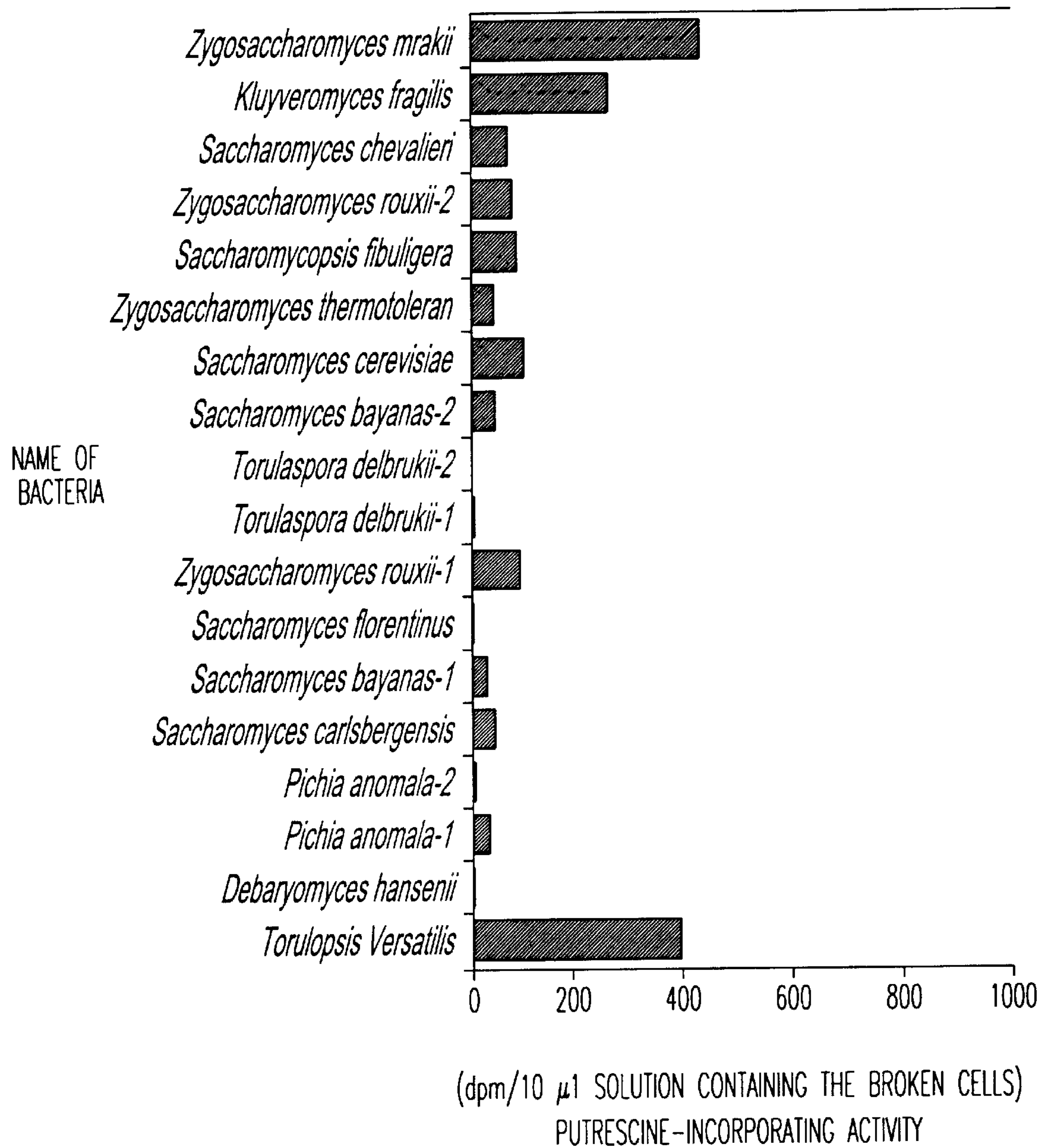
FIG. 4 shows putrescine-incorporating activity of a yeast used for foods and also yeast of the same genus in the solid culture.
Figure 5:
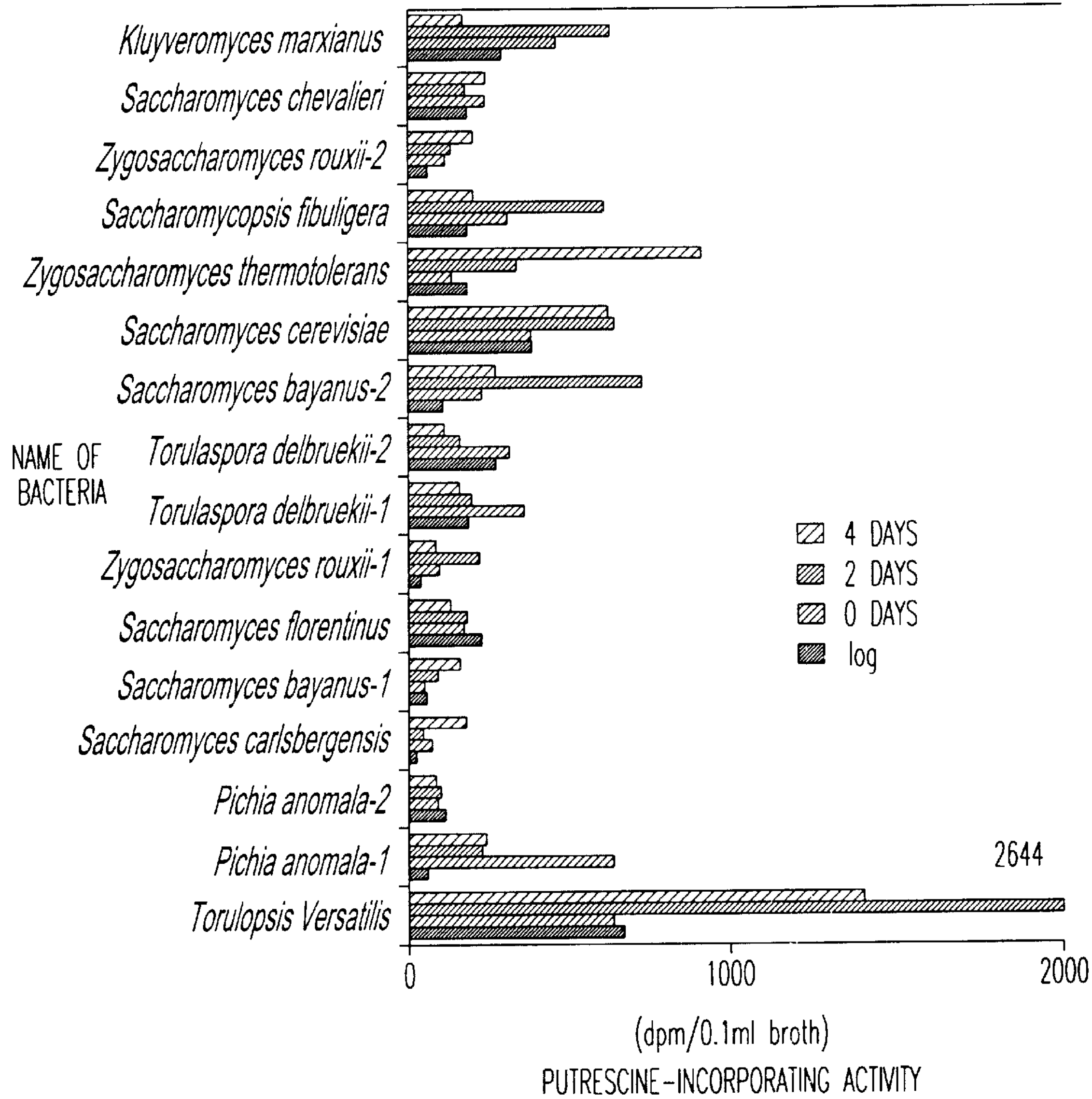
FIG. 5 shows putrescine-incorporating activity of a yeast used for foods and also yeast of the same genus in the liquid culture.
Figure 6:
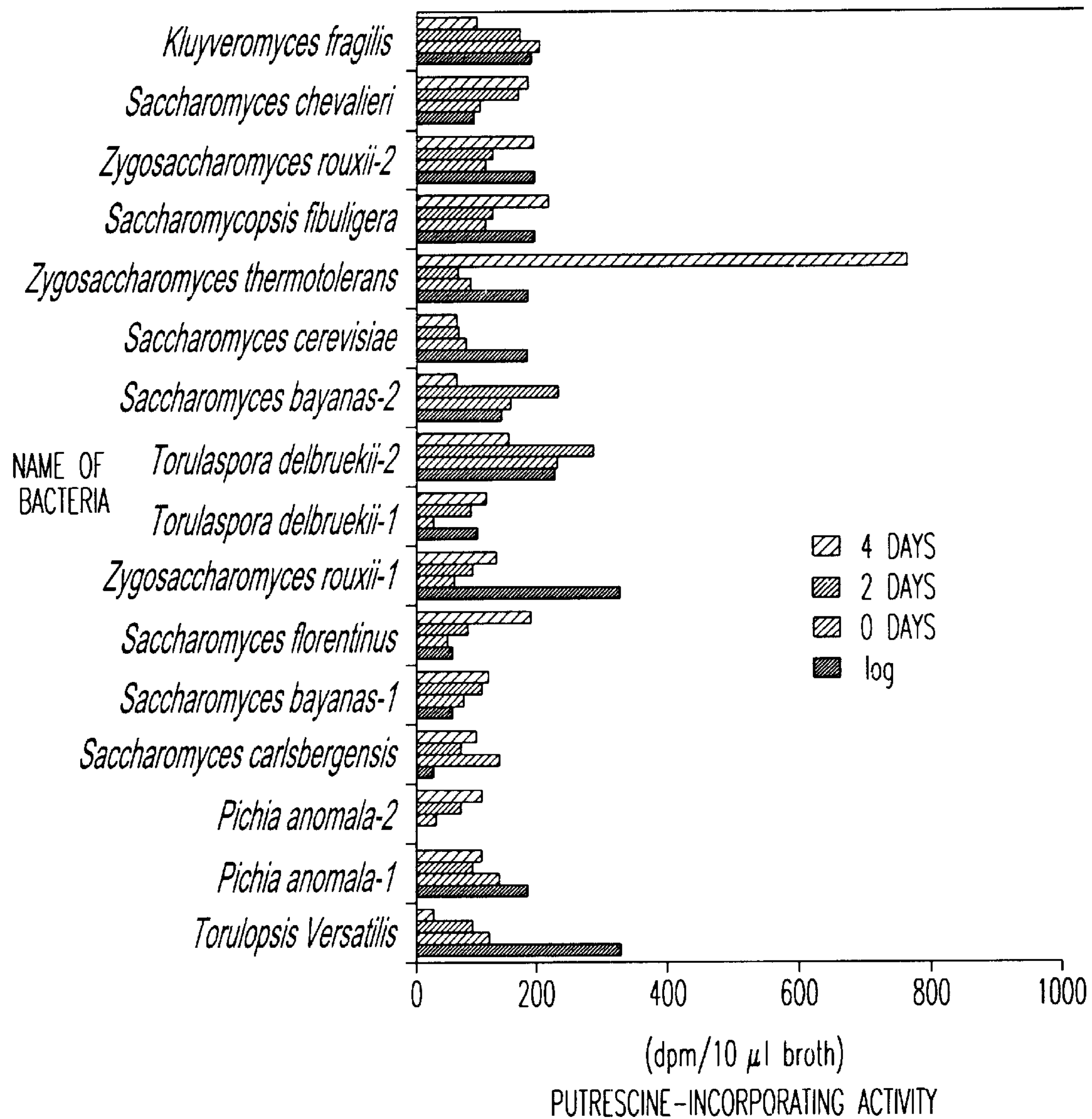
FIG. 6 shows the activity of incorporating putrescine in a supernatant liquid in the liquid culture of yeast used for foods and also yeast of the same genus.

The results of the determination of the strain samples in the liquid culture and solid culture are shown in FIGS. 4 to 6.

As shown in FIGS. 4 to 6, the putrescine-incorporating activity was recognized in the cells of yeasts of the genus Candida, Torulaspora, Saccharomyces, Zygosaccharomyces, Saccharomycopsis, Kluyveromyces, and Pichia or in the culture liquid thereof. Among them, *Candida versatilis, Pichia anomala, Saccharomyces cerevisiae, Zygosaccharomyces thermotolerans, Saccharomycopsis fibuligera, Torulaspora delbruekii* and *Kluyveromyces marxianus* had a high putrescine-incorporating activity.

EXAMPLE 3

In this Example, strains of filamentous fungi or the like usable for various foods, shown in the following Table 3, were used.

TABLE 3

| | |
|---|---|
| *Penicillium caseicolum* | IFO5849 |
| *Penicillium citrinum* | ATCC9849 |
| *Penicillium roqueforti* | IFO4622 |
| *Aspergillus sojae* | RIB1045 |
| *Aspergillus oryzae* | ATCC11494 |
| *Aspergillus tamari* | JCM2259 |
| *Aspergillus usamii* | IAM2185 |
| *Aspergillus glaucus* | IAM2124 |
| *Aspergillus saitoi* | IAM2190 |
| *Aspergillus niger* | ATCC16404 |
| *Mucor circinelloides* | ATCC15242 |
| *Rhizomucor pusillus* | IFO4578 |
| *Monascus purpureus* | ATCC16360 |
| *Rhizopus chinensis* | JCM5596 |
| *Rhizopus delemar* | JCM5564 |
| *Rhizopus javanicus* | JCM5574 |
| *Rhizopus japonicus* | AJ6076 |
| *Rhizopus oryzae* (1) | FERM BP-5549 |
| *Rhizopus oryzae* (2) | FERM BP-5546(AJ6168) |

In the above Table, RIB is an abbreviation of National Research Institute of Brewing (the same shall apply hereinafter).

The bacteria of the above-listed strains were cultured as follows: The liquid static culture was conducted by using a YM medium (comprising 5 g/l of peptone, 3 g/l of yeast extract, 3 g/l of malt extract and 10 or 200 g/l of glucose), and the liquid shaking culture was conducted by using an EPS medium (comprising 3 g/l of soy bean meal, 3 g/l of Pharmamedia, 10 g/l of soluble starch, 3 gll of yeast extract, 3 g/l of NZamine type A, 2 g/l of $CaCO_3$ and 10 or 40 g /1 of glucose, pH 6.5). The culture temperature was 25°. In the static culture, the cells were collected on the third, seventh and eleventh days. In the shaking culture, 10 ml of the culture liquid was taken and centrifuged to divide it into the supernatant liquid and cells on the third, fifth and seventh days.

The cells thus obtained were suspended in 5 to 10 ml of Tris buffer solution (20 mM Tris, pH 7.5) and broken with glass beads. The putrescine-incorporating activity of each of (1) the solution obtained by the static culture and containing the broken cells, (2) the solution obtained by the shaking culture and containing the broken cells and (3) supernatant liquid obtained by the shaking culture was determined in the same manner as that of Example 1.

Figure 7:
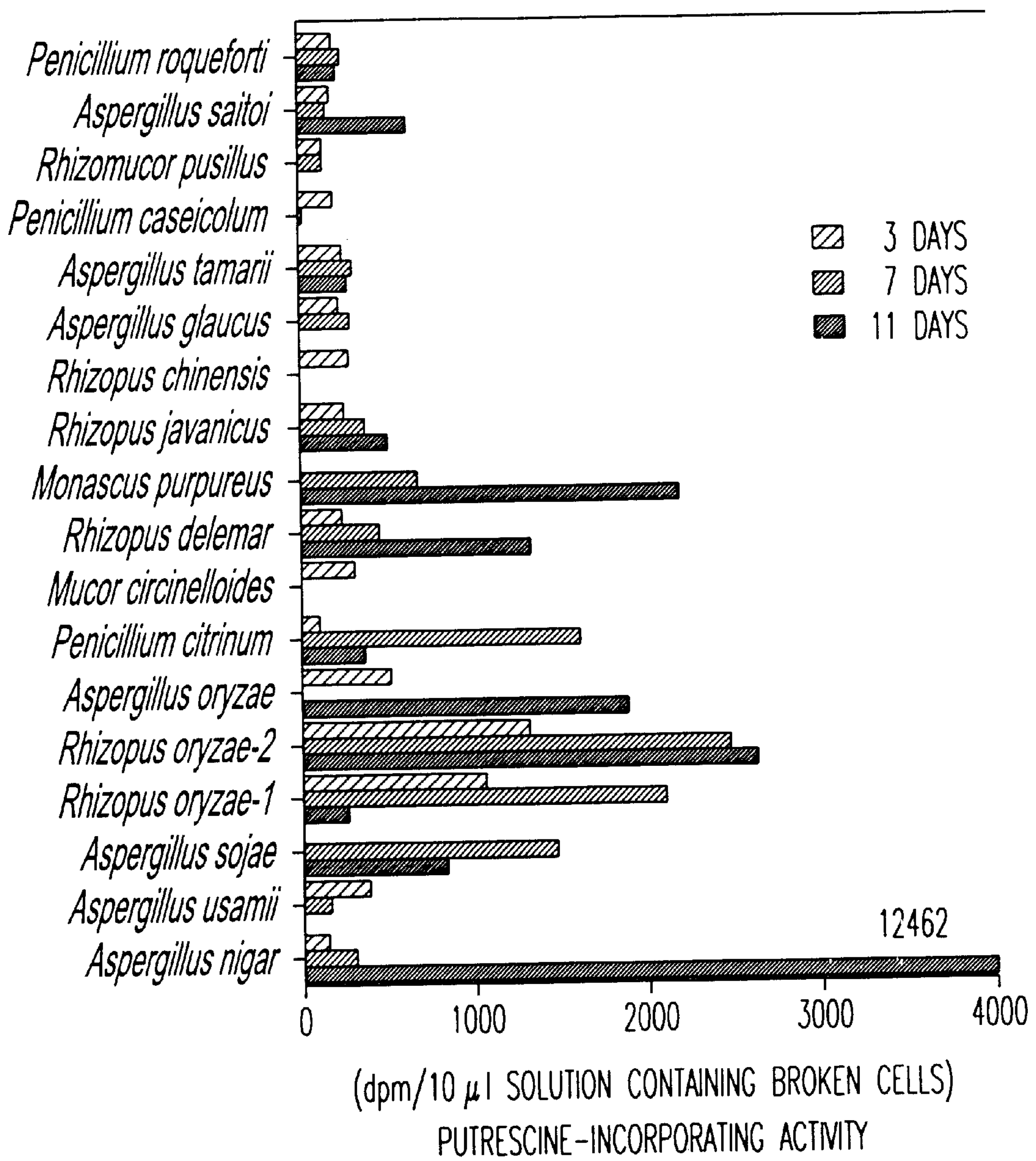
FIG. 7 shows putrescine-incorporating activity of cells in the liquid static culture of a filamentous fungus used for foods and also another filamentous fungus of the same genus.
Figure 8:
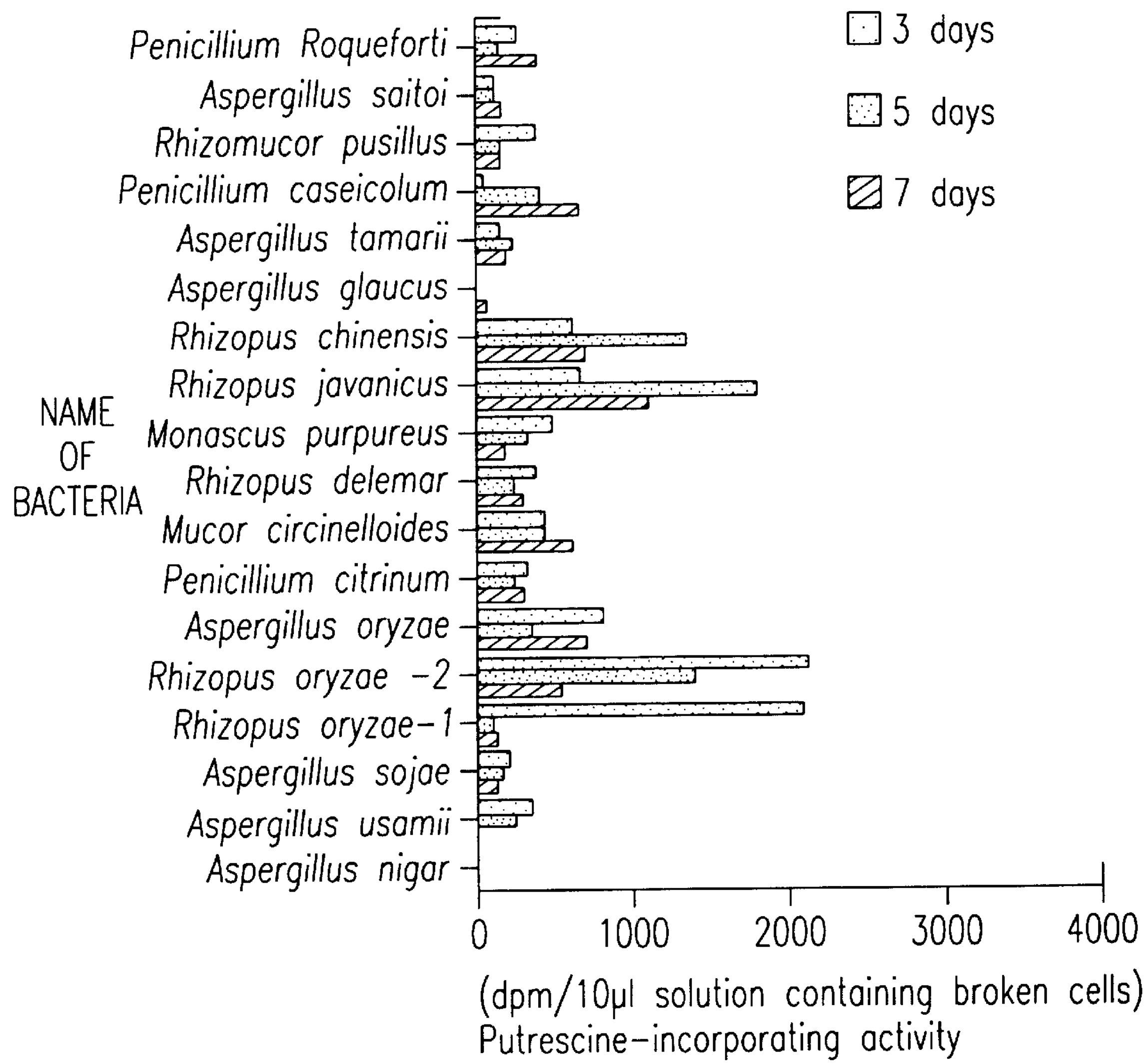
FIG. 8 shows putrescine-incorporating activity of cells in the liquid shaking culture of a filamentous fungus used for foods and also another filamentous fungus of the same genus.
Figure 9:
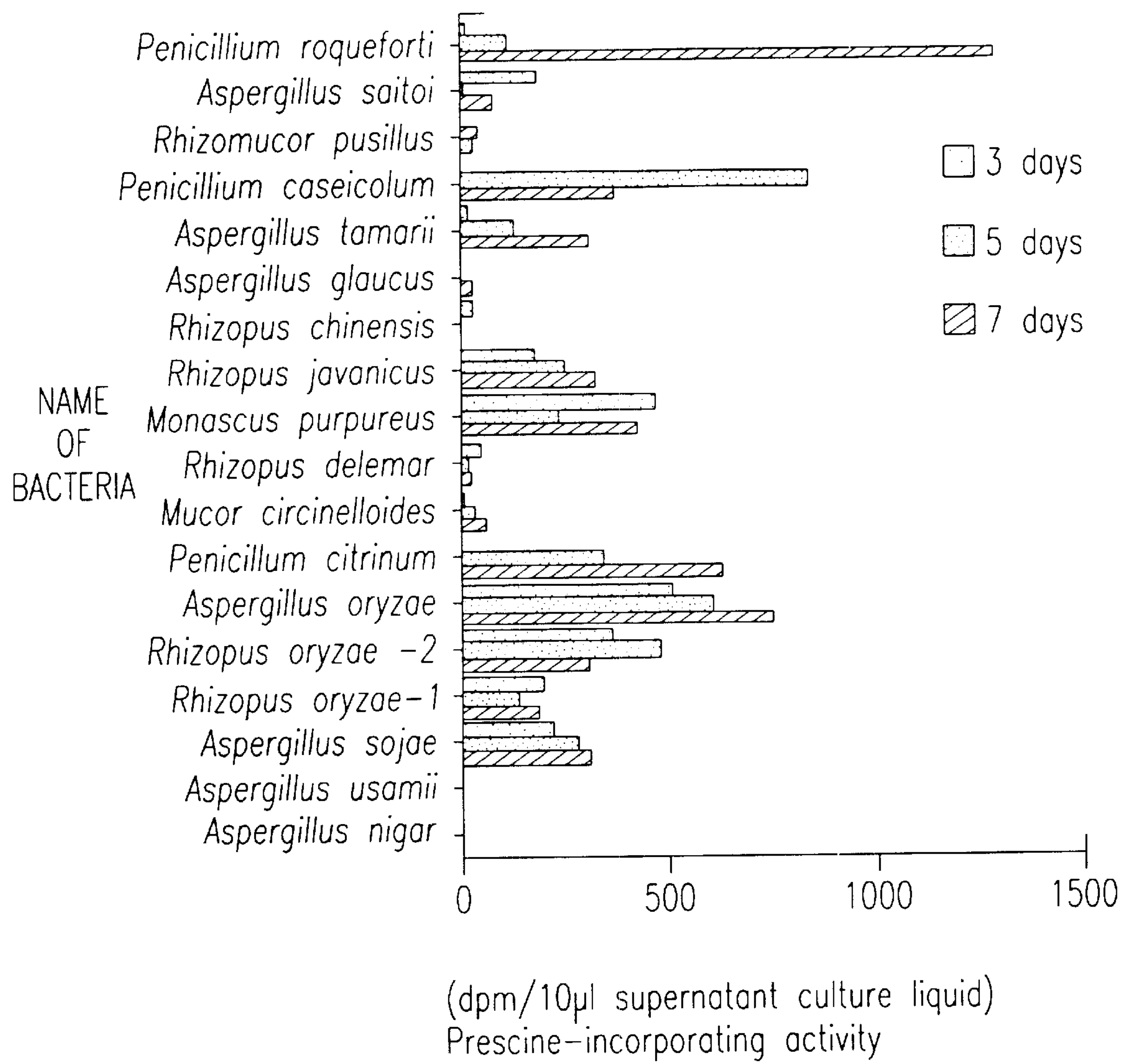
FIG. 9 shows putrescine-incorporating activity of filamentous fungus used for foods and also another filamentous fungus of the same genus in a supernatant liquid in the liquid shaking culture.

As shown in FIGS. 7 to 9, the putrescine-incorporating activity was recognized in the filamentous fungi of the genus Aspergillus, Penicillium, Rhizopus, Monascus, Mucor and Rhizomucor.

Among them, *Aspergillus saioti, Rhizopus oryzae, Rhizopus chinensis, Rhizopus delemar, Rhizopus javanicus, Penicillium citrinum, Mucor circinelloides, Rhizomucor pusillus* and *Monascus purpureus* had a relatively high putrescine-incorporating activity.

Referential Example 1

*Chlorella pyrenoidosa* NIES-226 and *Chlorella vulgaris* which belong to single-cell Chlorophyta were cultured by the shaking culture in a medium for chlorella [comprising 0.15 g/l of $Ca(NO_3)_2.4H_2O$, 0.1 g/l of $KNO_3$, 50 mg/l of sodium glycerophosphate, 40 mg/l of $MgSO_4.7H_2O$, 0.1 g/l of vitamine $B,_{12}$, 0.1 g/l of biotin, 0.01 mg/l of thiamine.HCl, 0.5 g/l of tris(hydroxymethyl)aminomethane, 3 ml/l of PIV metals at pH 7.5, wherein the PIV metals were 0.196 g/l of $FeCl_3.6H_2O$, 36 mg/l of $MnCl_2.4H_2O$, 22 mg/l of $ZnSO_4.7H_1O$, 4 mg/l of $CoCl_2.6H_2O$, 2.5 mg/l of $MoO_4.2H_2O$ and 1 g/l of $Na_2EDTA.2H_2O$ ] at 25° and 3000 1× the light period was 12 hours and the dark period was 12 hours). On the 14th day, 5 ml of the culture liquid was centrifuged to obtain the cells. The cells were suspended in 1 ml of Tris buffer solution (20 mM Tris, pH 7.5) and broken with glass beads. The suspension containing the broken cells was subjected to the test of the putrescine-incorporating activity in the same manner as that of Example 1.

The test results indicated that these kinds of chlorellas had the putrescine-incorporating activity as shown in Table 4.

TABLE 4

| Strain | Putrescine-incorporating activity (dpm) |
|---|---|
| *Chlorella pyrenoidosa* | 881 |
| *Chlorella vulgaris* | 156 |

Referential Example 2

Edible Basidiomycetous microorganisms were mainly used for the research. Both commercial and natural Basidiomycetous microorganisms were used.

About 2 g of the fruit bodies were cut into small pieces. 10 ml of Tris buffer solution (20 mM Tris, pH 7.5) was added thereto and they were broken with a homogenizer and then with glass beads. The broken cells of the fruit bodies were subjected to the test of the putrescine-incorporating activity in the same manner as that of Example 1. The results are shown in FIG. 10.

Figure 10:
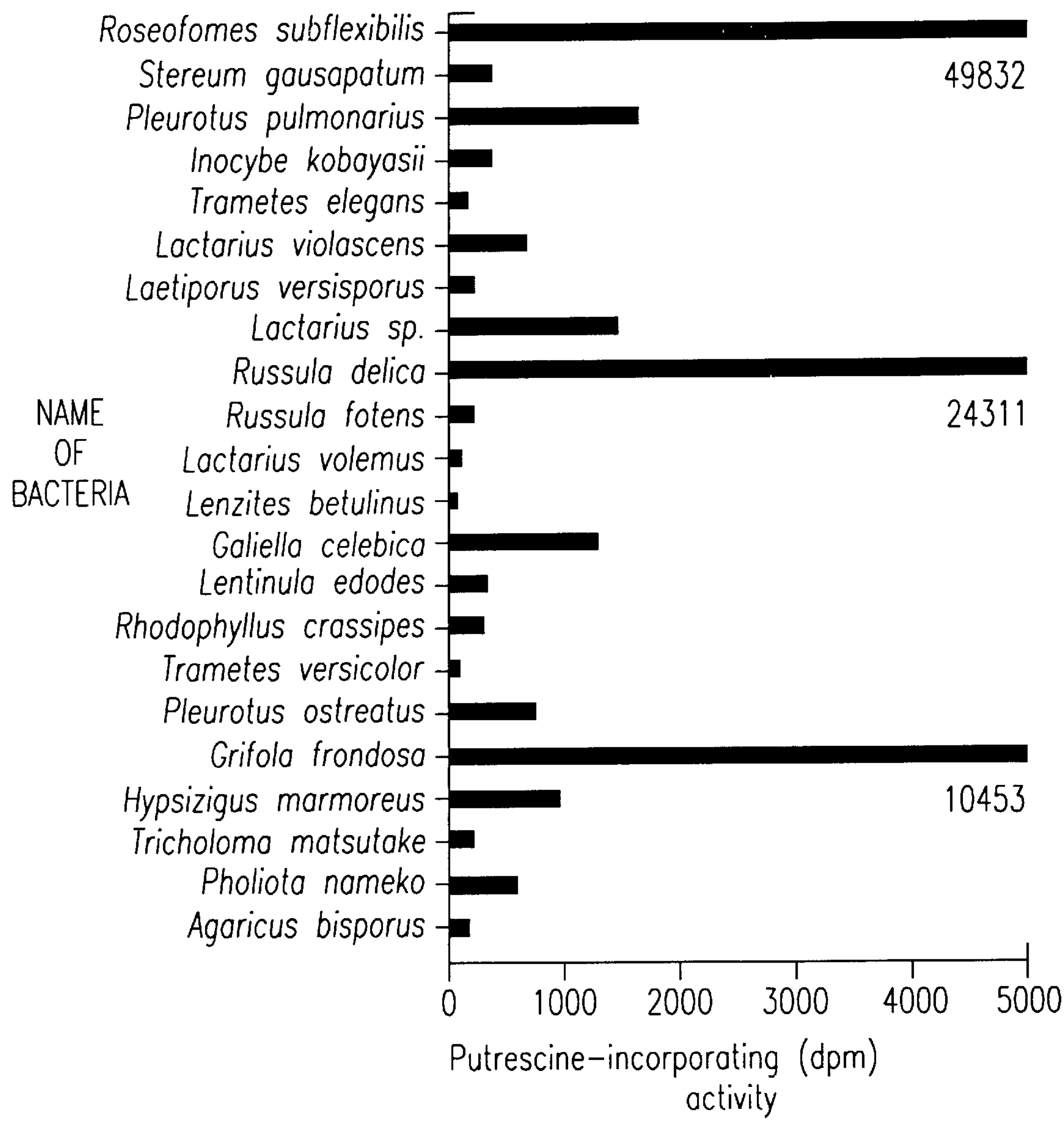
FIG. 10 shows putrescine-incorporating activity of a suspension containing broken cells of Basidiomycota.

As shown in FIG. 10, various Basidiomycetes microorganisms had the putrescine-incorporating activity.

*Roseofomes subflexibilis, Russula delica* and *Grifola frondosa* had particularly strong activity.

Referential Example 3:

Change of the Putrescine-incorporating Activity with Temperature

The TG activity was determined by determinating the putrescine-incorporating activity into dimethylcasein as described above. It is known that the crosslinked structure formed by TG can be formed by a physicochemical factor. In particular, it is known that the crosslinked structure is formed by heat. Therefore, depending on the conditions, the non-enzymatic incorporating activity might be detected. In addition, putrescine is incorporated into dimethylcasein by the dehydration-bonding or transition reaction of protease, and this effect might be detected as an apparent TG activity. Under the circumstances, the following tests were conducted.

1) change of the putrescine-incorporating activity with temperature,
2) change of the putrescine-incorporating activity with pH, and
3) putrescine-incorporating activity of commercial protease.

The change of the putrescine-incorporating activity with temperature was examined at first.

The same reaction solution as that of Example 1 (except that it did not contain the sample used as the enzyme source) was conducted at 30, 40, 50, 60, 70, 80 and 90° C. for 30 minutes. The amount of putrescine incorporated into dimethylcasein was determined with a liquid scintillation counter in the same manner as that of Example 1.

TABLE 5

| Temp. (° C.) | 30 | 40 | 50 | 60 | 70 | 80 |
|---|---|---|---|---|---|---|
| Putrescine-incorporating activity (dpm) | 231 | 322 | 507 | 816 | 1526 | 3183 |

It is apparent from Table 5 that the putrescine-incorporating activity is increased as the temperature is elevated even in the absence of TG.

Referential Example 4

Change of the Putrescine-incorporating Activity with pH, and

The same reaction solution as that of Example 1 (provided that it did not contain the sample used as the enzyme source) was conducted at varied reaction pH of 7, 8, 9, 10 or 11. The amount of putrescine incorporated into dimethylcasein was determined with a liquid scintillation counter in the same manner as that of Example 1.

TABLE 6

| pH | 7 | 8 | 9 | 10 | 11 |
|---|---|---|---|---|---|
| Putrescine-incorporating activity (dpm) | 310 | 367 | 707 | 1460 | 7094 |

It is apparent from the results shown in Table 6 that the putrescine-incorporating activity was increased as pH was elevated even in the absence of TG.

The results obtained in Referential Examples 3 and 4 suggest that when the TG activity and properties of a sample are examined, it is important to take the examination under the same reaction conditions.

Referential Example 5

Determination of Putrescine-incorporating Activity of Commercial Protease Specimen Trypsin (T-8253; a product of Sigma Co., Ltd.), α-chymotrypsin (C-7762; Sigma Co., Ltd.), subtilisin (P-5380; Sigma Co., Ltd.) and papain (P-4762; Sigma Co., Ltd.) were used as the enzyme sources.

As for the reaction conditions, the reaction was conducted in the presence of 0.1 M of Tris-HCl (pH 7.5), 6.3 mg/ml of dimethylcasein, 0.2 mM of putrescine dihydrochloride 1,4-$^{14}C$, 1 mM of $CaCl_2$ and 2 mM of DTT at 37° C. for 30 minutes. The amount of the enzyme added was 0.1 μg.

Figure 11:
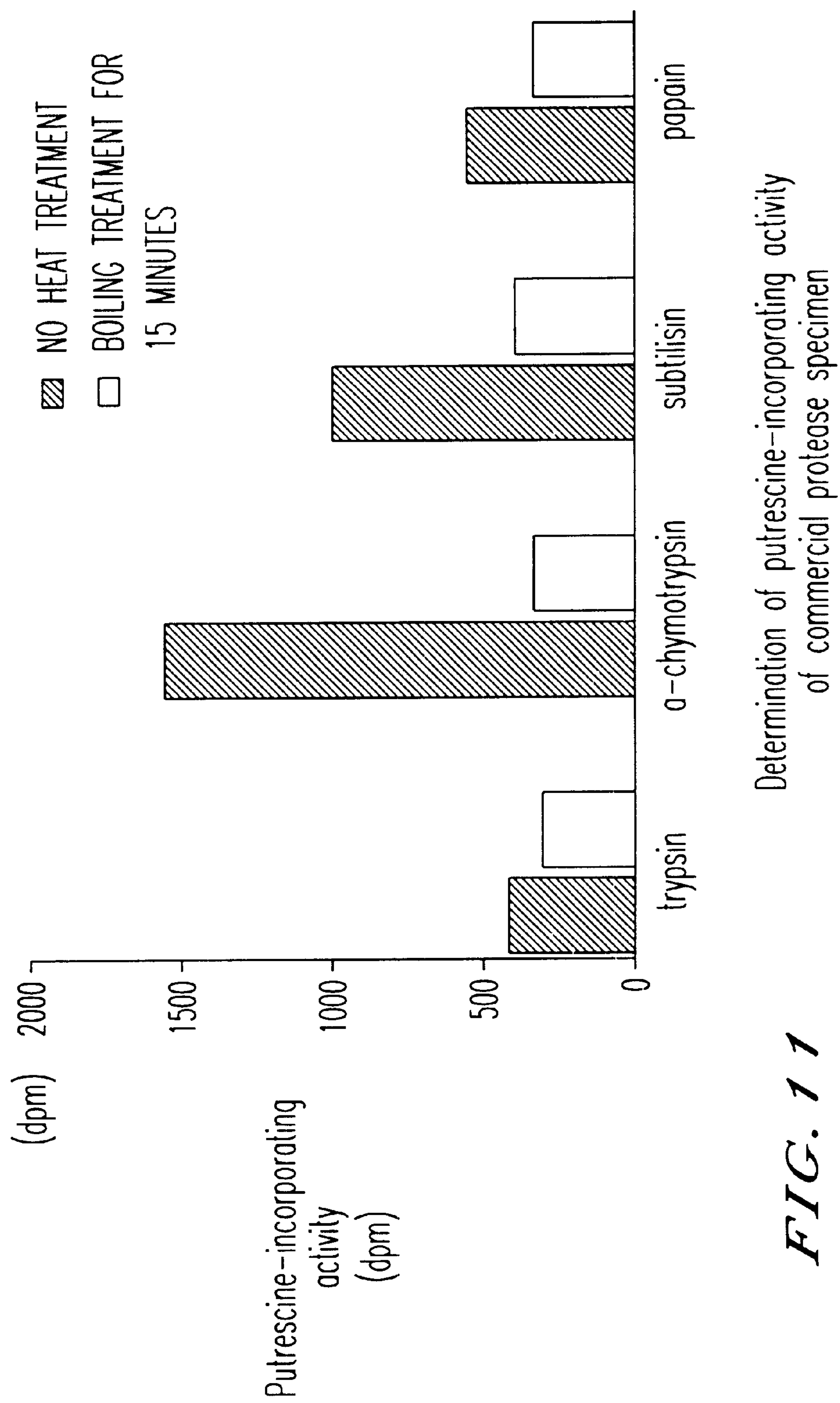
FIG. 11 shows putrescine-incorporating activity of a commercially available protease.

The results are shown in FIG. 11. It was understood from the results that all the commercial protease specimens thus tested had the putrescine-incorporating activity. Since protease itself has a weak putrescine-incorporating activity, it was suggested by this assay that not only the TG activity but other enzymatic activities such as protease activity would be also detected.

Therefore, the relationship between the putrescine-incorporating activity and protease activity was examined in detail by using ordinary TG derived from microorganisms, commercial protease and screening samples used in this experiment.

EXAMPLE 4

Effect of Protease Inhibitor on Putrescine-incorporating Activity

A TG enzyme preparation derived from Streptoverticillium (hereinafter referred to as "BTG), α-chymotripsin (C-7762; a product of Sigma Co., Ltd.) and a supernatant liquid obtained by the culture of *Aspergillus oryzae* were used as the enzyme sources. The culture supernatant liquid of *Aspergillus oryzae* used as the sample was obtained by concentrating the supernatant liquid obtained by the culture of *Aspergillus oryzae* ATCC 11494 (a sample used for the screening and shown in Table 3) with an ultrafilter.

The protease inhibitors used were soybean trypsin inhibitor (T-9003 of Sigma Co., Ltd.; hereinafter referred to as "STI"), soybean Bowman-Birk inhibitor (T-9777 of Sigma Co., Ltd.; hereinafter referred to as "BBI"), chymostatin (C-7268 of Sigma Co., Ltd.; hereinafter referred to as "CYM"), ovomucoid (T-2011 of Sigma Co., Ltd.; hereinafter referred to as "OVM") and ovoinhibitor (T-1886 of Sigma Co., Ltd.; hereinafter referred to as "OVI").

The enzyme source was treated with the protease inhibitor by mixing the enzyme source with each protease inhibitor and leaving the obtained mixture to stand on ice for 30 minutes before the determination of the putrescine-incorporating activity. In the determination of the putrescine-incorporating activity, 0.02 /ug of BTG, 0.1 μg of α-chymotripsin or 0.2 μg of supernatant protein obtained by the culture of *Aspergillus oryzae* was used for each sample. The amount of each protease inhibitor was 20 μg per sample.

Figure 12:
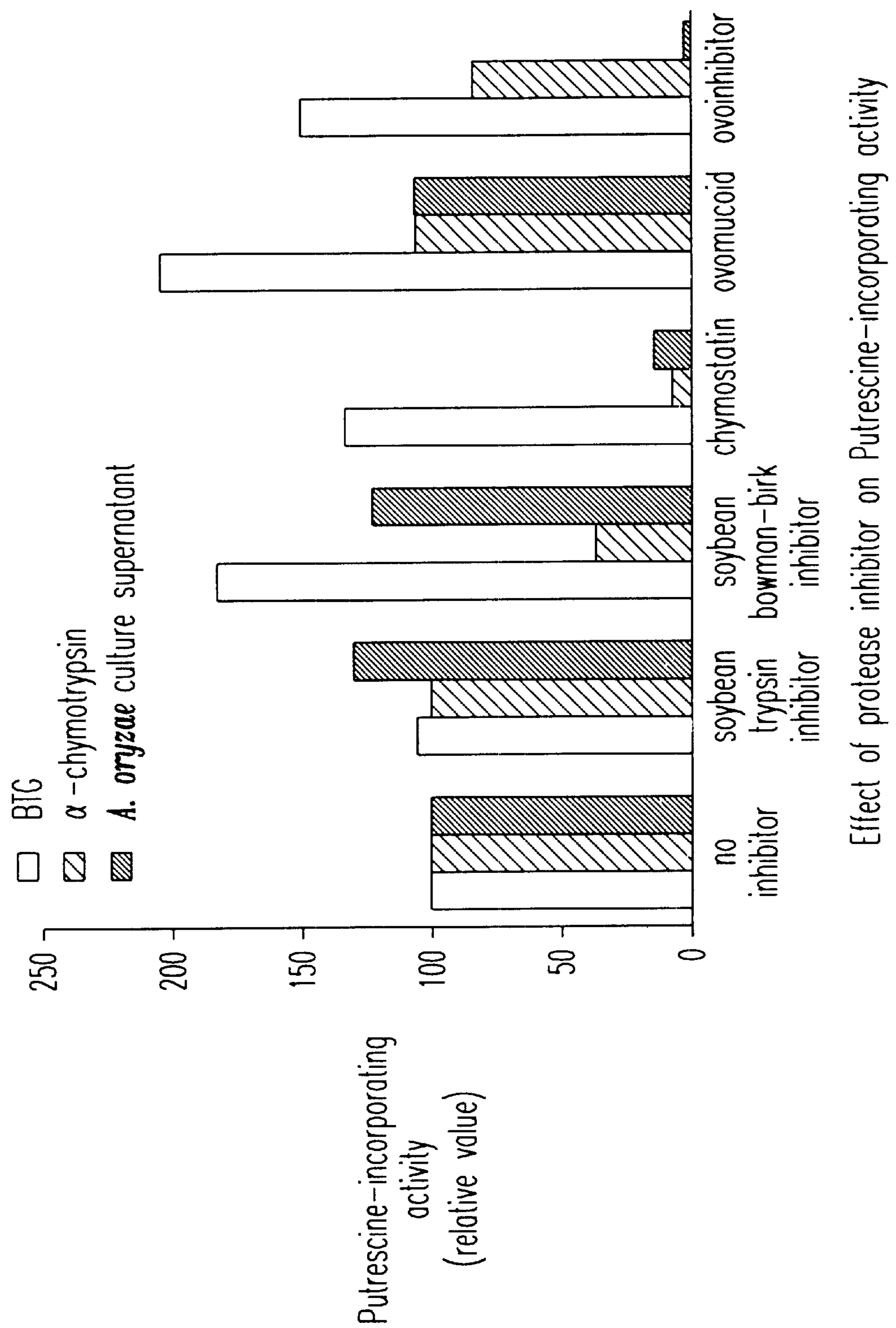
FIG. 12 shows the effect of a protease inhibitor on the putrescine-incorporating activity.

The results of the determination are shown in FIG. 12. The activity thus determined is given in terms of the relative value (the putrescine-incorporating activity obtained without using any inhibitor being 100). When BTG was used, no inhibition by any inhibitor was observed. However, (α-chymotripsin was seriously inhibited by BBI and CYM. When the supernatant liquid obtained by the culture of *Aspergillus oryzae* was used as the enzyme source, the serious inhibition was caused by CYM and OVI.

The fact that the inhibitor used has a high specificity to protease suggested that the putrescine-incorporating activity of α-chymotripsin and the culture supernatant liquid of *Aspergillus oryzae* is due to protease.

EXAMPLE 5

Effect of Protease Inhibitor on Protease Activity of α-chymotripsin and the Culture Supernatant Liquid of *Aspergillus oryzae*

The protease activity inhibition tests were conducted by using α-chymotripsin and the culture supernatant liquid of *Aspergillus oryzae* ATCC 1 1494 in the same manner as that of the above-described inhibition tests on the putrescine-incorporating activity as follows:

Protease activity was determined as follows: 0.2 ml of 5% (w/v) azo casein and 0.05 ml of 1 M Tris-HCl (pH 7.5) were added to 0.25 ml of the sample. After conducting the reaction at 37° C. for 30 minutes, 0.5 ml of 5% (w/v) trichloroacetic acid was added to the reaction mixture to terminate the reaction. The solution was centrifuged to remove the precipitates. The quantity of the azo dye in the supernatant liquid was determined by determining the absorbance at 366 nm, from which the protease activity of the sample was estimated.

The enzyme source and the inhibitor were added to 0.25 ml of the sample. The amounts of the enzymes were: 1 μg of α-chymotripsin and 1.6 μg of the protein in the culture supernatant liquid of *Aspergillus oryzae*. The amount of the inhibitor was 50 μg in all the cases. After mixing the inhibitor with the enzyme, the obtained mixture was left to stand on ice for 30 minutes before the determination of the protease activity.

Figure 13A:
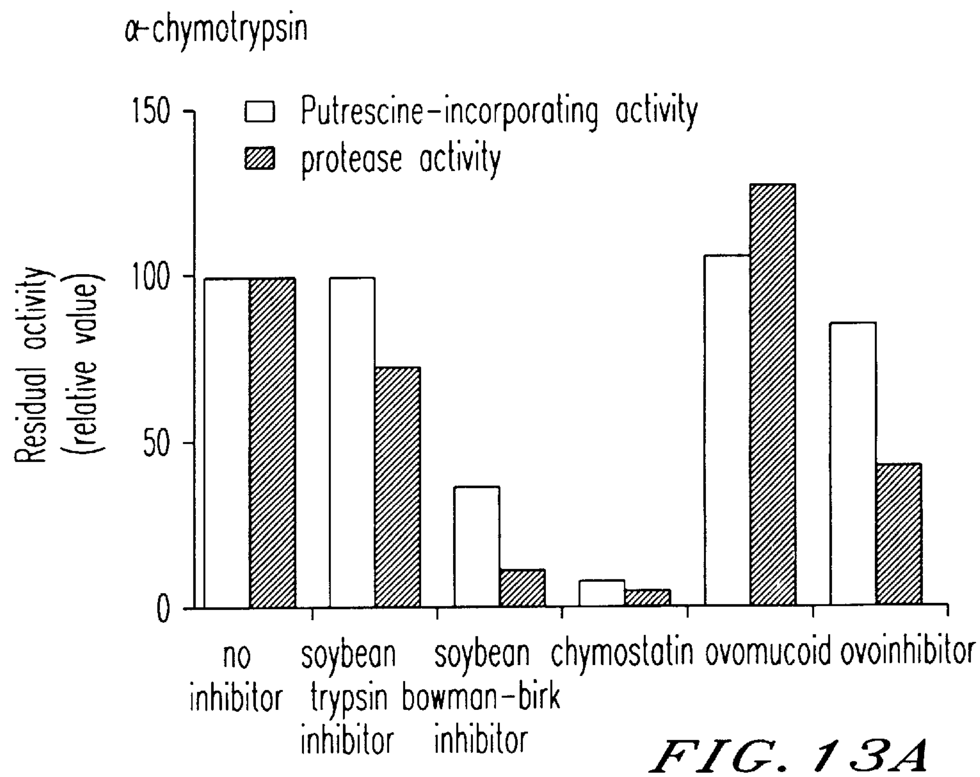
FIG. 13 shows the effect of a protease inhibitor on the protease activity in a supernatant liquid in the culture of α-chymotrypsin and *Aspergillus oryzae.*
Figure 13B:
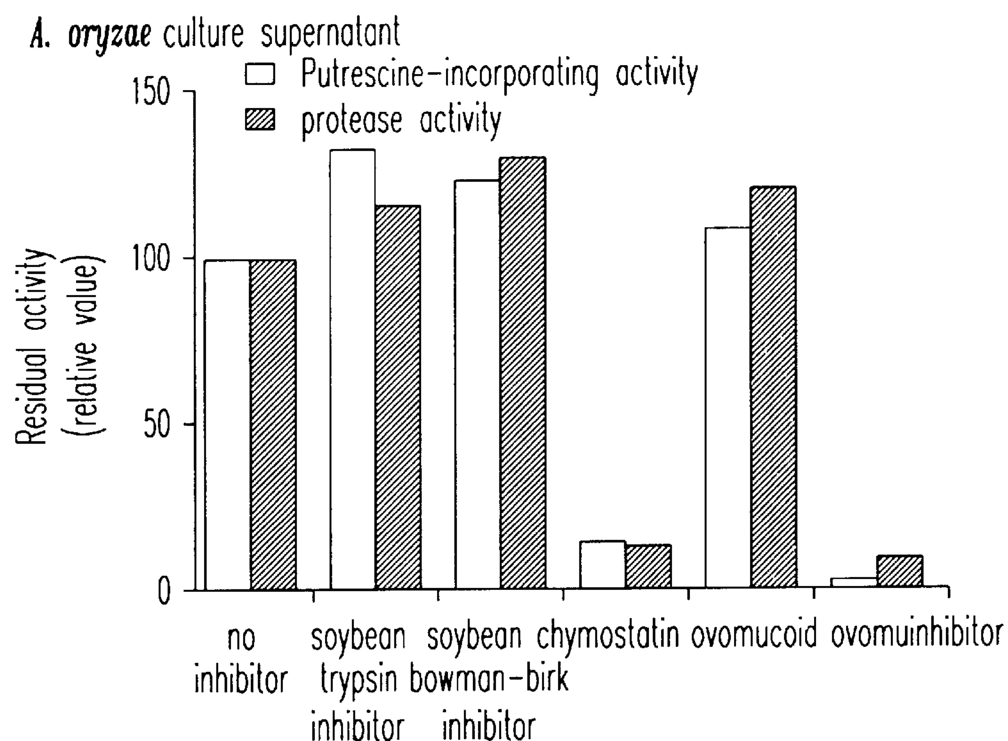

The results of the determination of the protease activity are shown in FIG. 13. The activity was given in terms of the relative value to the protease activity (100) obtained without the inhibitor. For the comparison with the putrescine-incorporating activity, the residual relative activity of the above-described putrescine-incorporating activity (see FIG. 12) is also shown.

As a result, α-chymotripsin or protease in the culture supernatant liquid of *Aspergillus oryzae* was inhibited by the same inhibitor as the protease inhibitor which inhibited the putrescine-incorporating activity. Namely, the protease activity of α-chymotripsin was specifically inhibited by BBI and CYM, and the protease activity of the culture supernatant liquid of *Aspergillus oryzae* was specifically inhibited by CYM and OVI.

These results supposedly indicate that the putrescine-incorporating activity of each of α-chymotripsin and the culture supernatant liquid of *Aspergillus oryzae* was due to protease contained in each of them.

From these findings, it is considered that the putrescine-incorporating activity of a given sample can be estimated to be derived from either protease or not, by determining the inhibition profiles of various protease inhibitors in the putrescine-incorporating activity as in that of the above-described α-chymotripsin or the culture supernatant liquid of *Aspergillus oryzae*. Namely, the putrescine-incorporating activity of TG itself is not inhibited by the protease inhibitor as in the case of BTG.

It is considered that the method for determining the putrescine-incorporating activity by combining the inhibition profiles of the protease inhibitors is a novel method by which only TG can be specifically selected unlike the conventional method wherein only the putrescine-incorporating activity is determined.

The above-described results indicate that the putrescine-incorporating activities obtained in Examples 1 to 3 and Referential Examples 1 and 2 might include those of other factors such as protease. On the basis of this idea, all the samples used for the experiments in Examples 1 to 3 and Referential Examples 1 and 2, namely the microorganisms shown in Tables 1 to 5, were tested again by the above-described, newly developed determination method. By this method, only the real TG excluding protease or the like could be selected.

EXAMPLE 6

Bacteria which produce only TG were specifically selected from all the samples shown in the above Tables 1 to 5 by a method described below.

The method for determining the putrescine-incorporating activity with the protease inhibitor was as described below. Unless otherwise stated, the activity-determination method in Example 1 was employed.

7 μl of water and 1 μl of 50 mM DTT were added to 10 μl of the sample. The thus-obtained mixture was left to stand on ice for 2 hours. Then 5 μl of a protease inhibitor solution was added thereto and the mixture was left to stand on ice for 30 minutes. The protease inhibitor solution used herein was 0.2 mg/ml of BBI, 0.2 mg/ml of CYM, 0.2 mg/ml of OVI, 0.2 mg/ml of STI or 0.2 mg/ml of OVM. After leaving to stand, the reagents were added so as to obtain the final concentration of 100 mM Tris (pH 7,5), 6.3 mg/ml of dimethylcasein and 1.2 μCi of 10 nM $^{14}$C-putrescine, and the quantity of the reaction liquid was controlled at 50 μl. After the reaction liquid was reacted at 37° C. for 30 minutes, TG activity was determined in the same manner as that of Example 1.

Some of the results of the determination are shown in Tables 7 and 8.

TABLE 7

Putrescine-incorporating activity (relative value)

| Strain | — | Inhibitor CYM | BBI | OVI | STI | OVM |
|---|---|---|---|---|---|---|
| *Micrococcus luteus* ATCC400 | 100 | 75 | 98 | 104 | 97 | 82 |
| *Clostridium acetobutylicum* ATCC4259 | 100 | 102 | 95 | 90 | 111 | 93 |
| *Candida versatilis* NRRL-Y6652 | 100 | 96 | 144 | 113 | 95 | 92 |
| *Monascus purpureus* ATCC16360 | 100 | 64 | 91 | 77 | 88 | 95 |
| *Rhizopus chinensis* JCM5596 | 100 | 100 | 131 | 86 | 115 | 90 |
| *Rhizopus delemar* JCM5564 | 100 | 88 | 91 | 66 | 75 | 98 |
| *Rhizopus javanicus* JCM5574 | 100 | 139 | 112 | 89 | 94 | 89 |
| *Rhizopus oryzae* (1) FERM BP-5549 | 100 | 80 | 101 | 84 | 121 | 93 |
| *Rhizopus oryzae* (2) FERM BP-5546 | 100 | 107 | 92 | 89 | 105 | 104 |

TABLE 8

Putrescine-incorporating activity (relative value)

| Strain | — | Inhibitor CYM | OVI |
|---|---|---|---|
| *Brevibacterium linens* ATCC9172 | 100 | 45 | 34 |
| *Kluyveromyces marxianus* IFF0288 | 100 | 195 | 28 |
| *Torulaspora delbruekii* CBS817 | 100 | 67 | 30 |
| *Saccharomyces bayanus* CBS395 | 100 | 0 | 98 |
| *Aspergillus sojae* RIB1045 | 100 | 31 | nt |
| *Penicillium citrinum* ATCC9849 | 100 | 21 | 33 |
| *Penicillium caseicolum* IFO5849 | 100 | 14 | nt |
| *Grifola frondosa* | 100 | 60 | 39 |

nt: not tested.

Table 7 shows examples of the samples having the putrescine-incorporating activity not strongly inhibited by the protease inhibitor. The putrescine-incorporating activity was not strongly inhibited by any of CYM, BBI and OVI. From this fact, it was judged that the activities of the microorganisms shown in Table 7 were the intrinsic TG activity.

Table 8 shows examples of the samples having the putrescine-incorporating activity strongly inhibited by the protease inhibitor. Samples prepared from, for example, *Brevibacterium linens, Saccharomyces bayanus, Aspergillus sojae, Penicillium citrinum, Penicillium caseicolum* or *Hypsizigus marmoreus* were inhibited by CYM to an extent of at least 50%. In the same manner, samples prepared from, for example, *Brevibacterium linens, Kluyveromyces marxianus, Torulaspora delbruekii, Penicillium citrinum* or *Grifola frondosa* were inhibited by OVI to an extent of at least 50%. From these results, the putrescine-incorporating activities of the samples shown in Table 8 were judged to be due to protease.

After the heat treatment conducted at 100° C. for 15 minutes, the samples prepared from the microorganisms such as *Zygosaccharomyces thermotolerans* CBS6340, *Aspergilllus saitoi* JAM2 190, Aspergillus nigar ATCC 16404 or *Russula delica* had a putrescine-incorporating activity equal to that before the heat treatment. It was judged, therefore, that the putrescine-incorporating activity of each of these samples is that caused by the non-specific adsorption of putrescine by the action of a substance contained in the samples.

After the experiments wherein the protease inhibitor was used for all the strains, microorganisms of the genus Micrococcus, Clostridium, Candida, Rhizopus and Monascus were selected as the microorganisms which are not inhibited by the protease inhibitors and which are free from the non-specific adsorption of putrescine.

Thus, the putrescine-incorporating activity of the samples derived from these microorganisms were judged to be the intrinsic TG activity.

In particular, the following microorganisms were judged to be useful for the TG production: *Micrococcus luteus, Clostridium acetobutylicum, Candida versatilis, Rhizopus oryzae, Rhizopus chinensis, Rhizopus delemar, Rhizopus javanicus* and *Monascus purpureus.*

EXAMPLE 7

The 101 liquid culture of *Candida versatilis* NRRL Y-6652 judged to be the TG-producing microorganism in Example 6 was conducted under the same conditions as those of Example 2. The cells were collected, washed, collected again and broken with beads. The suspension of the broken cells was centrifuged, and the supernatant liquid was subjected to the ion exchange chromatography with Q Sepharose (Pharmacia Aktiebolag). After the elution with 0 M to 1 M NaCl followed by the fractionation, a fraction having the TG activity was concentrated by the ultrafiltration. After reacting in casein solution (10% casein, 25 mM Tris, pH 7.5, 5 mM DTT) containing a 20% solution of this fraction at 37° C. for 24 hours, the gelation of the reaction solution could be confirmed.

According to the present invention, TG can be produced from microorganisms having the following three advantages: (1) low cost, (2) high growth rate and (3) being used for foods from old times. Since TG thus obtained is capable of producing gelled protein, it is usable for producing various foods such as yoghurts, cheeses and boiled fish pastes.

*Rhizopus oryzae* AJ 6158 described in this specification was deposited with the National Institute of Bioscience and Human-Technology Agency of Industrial Science and Technology, Ministry of International Trade and Industry (1-3, Higashi 1-chome, Tsukuba city, Ibaraki Prefecture, Japan) to be preserved with nomination of FERM No. P-15022 on Jul. 3, 1995, and then deposited with nomination of FERM BP-5549 according to the demand of the transfer to the deposition according to the Budapest Treaty on May 27, 1996. *Rhizopus oryzae* AJ 6168 was also deposited in the National Institute of Bioscience and Human-Technology Agency of Industrial Science and Technology, Ministry of International Trade and Industry (1-3, Higashi 1-chome, Tsukuba city, Ibaraki Prefecture, Japan) to be preserved with nomination of FERM BP-5546 on May 23, 1996.

What is claimed is:

1. A process for producing an intrinsic transglutaminase, which comprises culturing a microorganism selected from the group consisting of *Micrococcus luteus, Clostridium acetobutylicum, Candida versatilis, Rhizopus oryzae, Rhizopus chinensis, Rhizopus delemar, Rhizopus javanicus* and *Monascus purpureus* in a medium to produce the transglutaminase in the medium or in the cells and isolating the transglutaminase.

2. A process for producing an intrinsic transglutaminase, which comprises culturing a microorganism selected from the group consisting of *Micrococcus luteus, Clostridium acetobutylicum, Candida versatilis, Rhizopus oryzae, Rhizopus chinensis, Rhizopus delemar, Rhizopus javanicus* and *Monascus purpureus* in a medium to produce the transglutaminase in the medium or in the cells, and isolating the transglutaminase (1) from the medium or (2) by breaking the cells.

3. The process of claim 1, wherein the microorganism is selected from the group consisting of *Micrococcus luteus* ATCC400, *Clostridium acetobutylicum* ATCC4259, *Candida versatilis* NRRL-Y6652, *Rhizopus oryzae* FERM BP-5546, *Rhizopus oryzae* FERM BP-5549, *Rhizopus chinensis* JCM5596, *Rhizopus delemar* JCM5564, *Rhizopus javanicus JCM*5574 and *Monascus purpureus* ATCC16360.

4. The process of claim 2, wherein the microorganism is selected from the group consisting of *Micrococcus luteus* ATCC400, *Clostridium acetobutylicum* ATCC4259, *Candida versatilis* NRRL-Y6652, *Rhizopus oryzae* FERM BP-5546, *Rhizopus oryzae* FERM BP-5549, *Rhizopus chinensis* JCM5596, *Rhizopus delemar* JCM5564, *Rhizopus javanicus* JCM5574 and *Monascus purpureus* ATCC16360.

* * * * *